US011944456B2

(12) United States Patent
Komada et al.

(10) Patent No.: US 11,944,456 B2
(45) Date of Patent: Apr. 2, 2024

(54) CERAMIC GUIDE, CERAMIC GUIDE DEVICE, AND CERMIC GUIDE MODULE

(71) Applicants: KYOCERA Corporation, Kyoto (JP); TOHOKU UNIVERSITY, Sendai (JP)

(72) Inventors: Daisuke Komada, Omihachiman (JP); Hajime Mushiake, Sendai (JP); Tomokazu Ohshiro, Sendai (JP)

(73) Assignees: KYOCERA Corporation, Kyoto (JP); TOHOKU UNIVERSITY (JP)

( * ) Notice: Subject to any disclaimer, the term of this patent is extended or adjusted under 35 U.S.C. 154(b) by 913 days.

(21) Appl. No.: 16/966,235

(22) PCT Filed: Jan. 31, 2019

(86) PCT No.: PCT/JP2019/003520
§ 371 (c)(1),
(2) Date: Jul. 30, 2020

(87) PCT Pub. No.: WO2019/151455
PCT Pub. Date: Aug. 8, 2019

(65) Prior Publication Data
US 2021/0045688 A1 Feb. 18, 2021

(30) Foreign Application Priority Data
Jan. 31, 2018 (JP) ................. 2018-015924

(51) Int. Cl.
*A61B 5/00* (2006.01)
(52) U.S. Cl.
CPC ........ *A61B 5/6847* (2013.01); *A61B 2503/40* (2013.01); *A61B 2503/42* (2013.01); *A61B 2560/04* (2013.01)

(58) Field of Classification Search
CPC .............. A61B 5/6847; A61B 2503/40; A61B 2503/42; A61B 2560/04
See application file for complete search history.

(56) References Cited

U.S. PATENT DOCUMENTS

| 2004/0082875 A1 | 4/2004 | Donoghue et al. |
| 2006/0079953 A1* | 4/2006 | Gregorich ............. A61F 2/3662 623/23.72 |

(Continued)

FOREIGN PATENT DOCUMENTS

| CN | 203662756 U | * | 6/2014 |
| CN | 206621358 U | | 11/2017 |

(Continued)

*Primary Examiner* — Linda C Dvorak
*Assistant Examiner* — Abigail Bock
(74) *Attorney, Agent, or Firm* — Volpe Koenig

(57) ABSTRACT

A ceramic guide device includes a columnar ceramic guide including a first portion including a first end, a second portion including a second end and having a smaller diameter than a diameter of the first portion, and a third portion disposed between the first portion and the second portion, the columnar ceramic guide provided with an insertion hole through which a long wire electrode can be inserted from the first end to the second end; and the long wire electrode that penetrates through the insertion hole, the long wire electrode including a first protruding portion projecting from the first end, and a second protruding portion projecting from the second end.

10 Claims, 16 Drawing Sheets

(56) References Cited

U.S. PATENT DOCUMENTS

| | | |
|---|---|---|
| 2011/0178422 A1 | 7/2011 | Tokuda et al. |
| 2012/0302857 A1* | 11/2012 | Yamakawa .......... A61B 5/6868 600/378 |
| 2013/0131461 A1 | 5/2013 | Jorge et al. |

FOREIGN PATENT DOCUMENTS

| | | |
|---|---|---|
| JP | 2010-540202 A | 12/2010 |
| JP | 5224482 B2 | 7/2013 |
| JP | 2017-113358 A | 6/2017 |
| WO | 2011/132756 A1 | 10/2011 |
| WO | 2012/017950 A1 | 2/2012 |

* cited by examiner

CERAMIC GUIDE, CERAMIC GUIDE DEVICE, AND CERMIC GUIDE MODULE

CROSS-REFERENCE TO RELATED APPLICATIONS

This application is a national stage entry according to 35 U.S.C. 371 of International Application No. PCT/JP2019/003520, filed on Jan. 31, 2019, which claims priority to Japanese Patent Application No. 2018-015924, filed on Jan. 31, 2018, the contents of which are entirely incorporated herein by reference.

TECHNICAL FIELD

The present disclosure relates to a ceramic guide, a ceramic guide device using the same, and a ceramic guide module, which can be used to insert a long insert such as a wire electrode, a tube, or a catheter into a living body such as the brain of a small animal and to fix the insert in place.

BACKGROUND

In the past, in order to record the neural activity from the brain of small animals, such as rodents including mice and rats, and marmosets, over a certain period of time, a long insert such as a wire electrode may be pierced and fixed in the brain. To fix the wire electrode in the living body, for example, methods of directly implanting a linear wire electrode made of stainless steel or a stainless alloy, which has relatively high rigidity, or fixing the wire electrode with a guiding component such as a screw have been adopted (See, for example, WO 2011/132756 (Patent Literature 1), WO 2012/017950 (Patent Literature 2), JP-A 2010-540202 (Patent Literature 3), and JP-B2 5224482 (Patent Literature 4)).

SUMMARY

Technical Problem

In the conventional techniques described in Patent Literatures 1 to 4 above, which utilize thick wire electrodes, a damage to the living tissues such as brain is severe, thus, these technologies are highly invasive to the living body. If a thin wire electrode is used instead to minimize such damage to living tissues, the rigidity of the wire electrode will be decreased and, so-called "stiffness" of the wire necessary to pierce a hard tissue such as dura mater is lost. Therefore, a technical problem arises, that the handling operability of the wires is reduced for the operator.

Further, in the conventional techniques described in Patent Literatures 2 and 4, the dimension of the guiding components for the electrodes into the brain tissue is large, and then, a craniotomy with manipulators is often necessary. Therefore, another problem arises that placing the electrode at a target position tends to be a large-scale procedure and it takes time. In addition, since the guiding component for the electrode is merely placed on the skull, stability of the electrodes in the living body is poor.

An object of the disclosure is to provide a ceramic guide, a ceramic guide device using this guide and a ceramic guide module, with which inserts such as wire electrodes can be stably placed and fixed into a living body with less burden to the living tissues.

Solution to Problem

A ceramic guide of the present disclosure is a ceramic guide to be fixed to a living body, including:

a columnar ceramic body provided with an insertion hole through which a long insert can be inserted from a first end to a second end of the columnar ceramic body, the columnar ceramic body including
  a first portion including the first end,
  a second portion including the second end and having a smaller diameter than a diameter of the first portion, and
  a third portion disposed between the first portion and the second portion.

A ceramic guide device of this disclosure is a ceramic guide device to be fixed to a living body, including:
  the ceramic guide mentioned above; and
  a long insert that penetrates through the insertion hole, the long insert including a first protruding portion projecting from the first end, and a second protruding portion projecting from the second end,
  the first protruding portion being connected to a predetermined external device,
  the second protruding portion being inserted into a living body.

A ceramic guide module of this disclosure includes the ceramic guide device; and
  a connector to which the long insert is connected.

BRIEF DESCRIPTION OF DRAWINGS

Objects, features, and advantages of the disclosure will be more apparent from the following detailed description and drawings.

DETAILED DESCRIPTION

Figure 1:
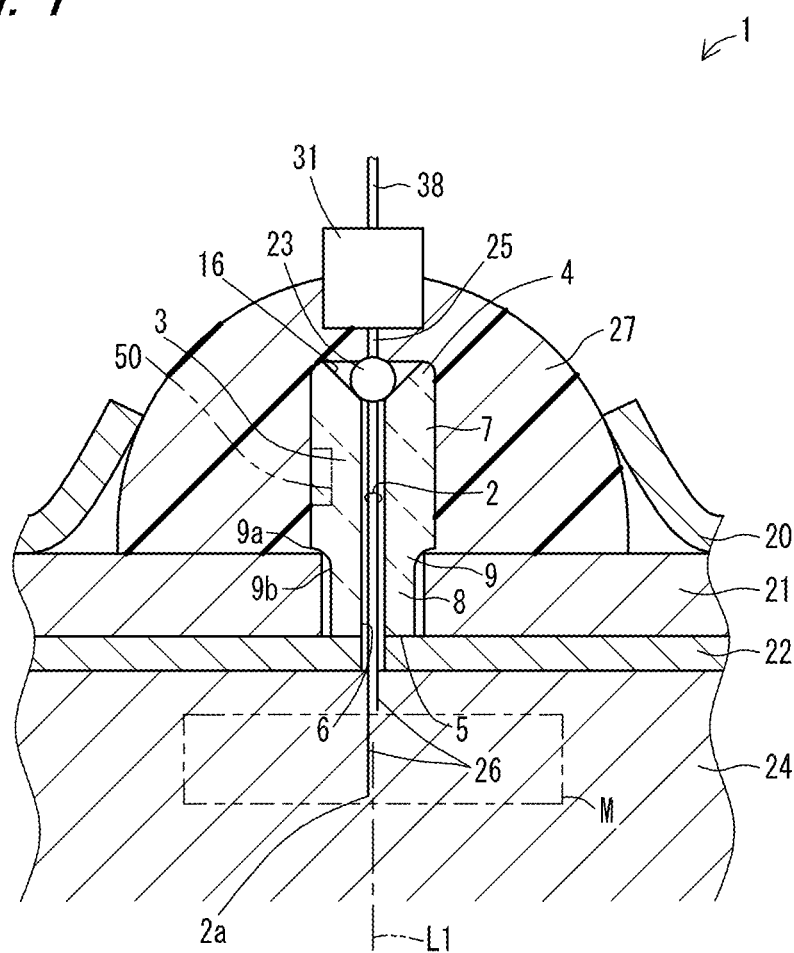
FIG. 1 is a partial cross-sectional view showing a ceramic guide device using a ceramic guide according to an embodiment of the disclosure.

Hereinafter, preferable embodiments of the disclosure will be described in detail with reference to the drawings. FIG. 1 is a partial cross-sectional view showing a ceramic guide device using a ceramic guide according to an embodiment of the disclosure. A ceramic guide device 1 of the present embodiment includes a wire electrode 2 which is an insert made of a filamentous elongated material in order to obtain information on nerve activity from the brain of a small experimental animal such as rodents and marmosets, and a ceramic guide 3 that is preferably used to place the wire electrode 2 inside the brain.

Figure 2:
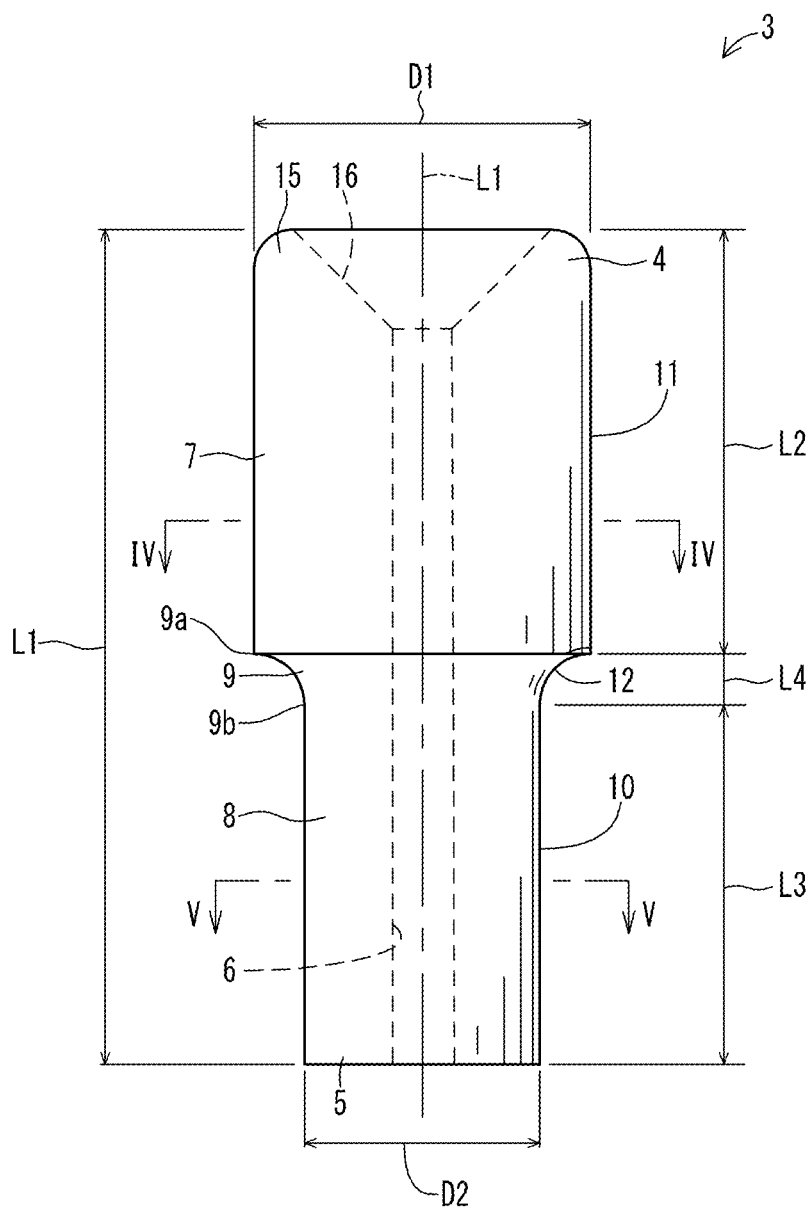
FIG. 2 is an enlarged side view of the ceramic guide.
Figure 3:
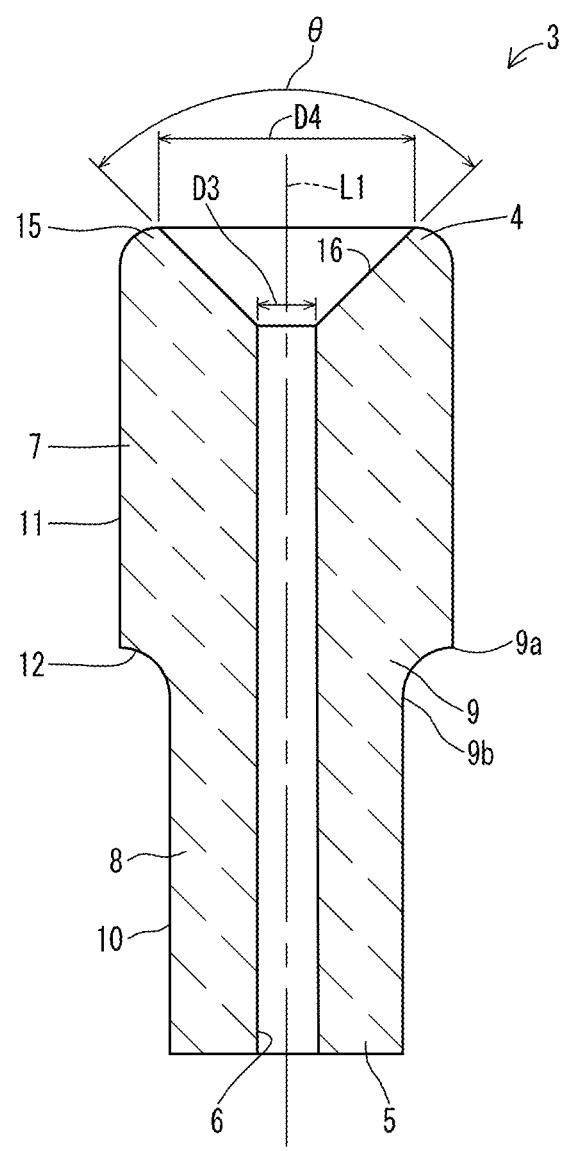
FIG. 3 is a cross-sectional view of the ceramic guide.
Figure 4:
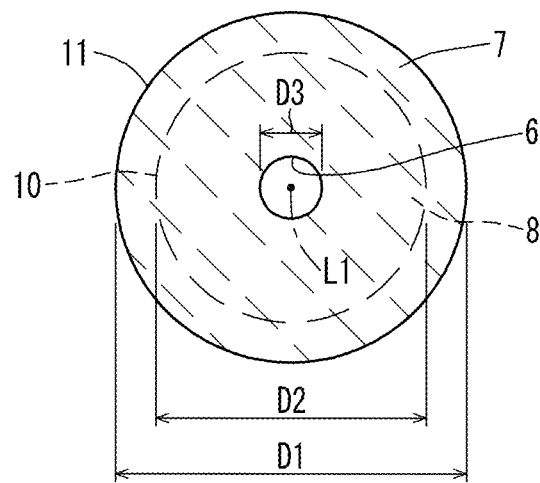
FIG. 4 is a cross-sectional view taken along the line IV-IV in FIG. 2.
Figure 5:
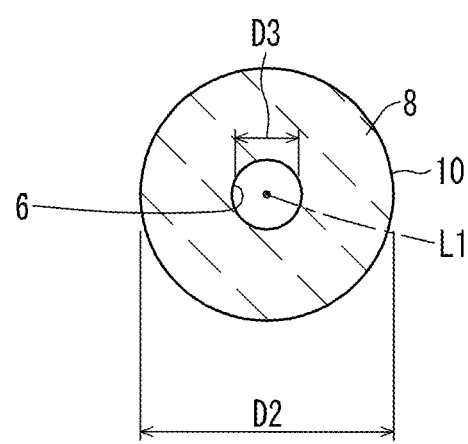
FIG. 5 is a cross-sectional view taken along the line V-V in FIG. 2.

FIG. 2 is an enlarged side view of the ceramic guide, and FIG. 3 is a cross-sectional view of the ceramic guide. FIG. 4 is a cross-sectional view taken along the line IV-IV of FIG. 2, and FIG. 5 is a cross-sectional view taken along the line V-V of FIG. 2. The ceramic guide 3 includes a columnar body provided with an insertion hole 6 into which the wire electrode 2 described above can be inserted and which penetrates from a first end 4 to a second end 5. The ceramic guide 3 includes a columnar ceramic body, and the ceramic body includes a first portion 7 including the first end 4, a second portion 8 including the second end 5 and having a smaller diameter than a diameter of the first portion 7, and a third portion 9 coaxially connected between the first portion 7 and the second portion 8. An outer peripheral surface 12 of the third portion 9 is curved in a direction approaching a central axis L1 from a peripheral edge 9a on the first portion 7 side to a peripheral edge 9b on the second portion 8 side. In this embodiment, the ceramic guide 3 and the ceramic body are substantially the same. In another embodiment, the outer peripheral surface 12 of the third portion 9 may have a shape inclined from the peripheral edge 9a on the first portion 7 side toward the peripheral edge 9b on the second portion 8 side in a direction approaching the central axis L1, that is, a shape that forms an outer peripheral surface of the inverted truncated cone.

The ceramic guide 3 is fixed in a state in which the second portion 8 penetrates through parts of the living body, for example, a scalp 20 and a skull 21 of a head of the small experimental animal, the third portion 9 works as a stopper, and the first portion 7 protrudes to the outside of the living body. When fixing the ceramic guide 3 to the head, the operator grips the first portion 7 of the ceramic guide 3 with tweezers and attaches the ceramic guide to the measurement target site of the head.

In order to facilitate mounting work of the ceramic guide 3 with such a technique using the tweezers, the outer peripheral surface 11 of the first portion 7 may be roughened in another embodiment. As a result, the gripping force of the ceramic guide 3 by the tweezers can be increased, displacement of the ceramic guide 3 with respect to the tweezers can be prevented, and thus, excellent handling performance can be achieved.

The wire electrode 2 is inserted into the insertion hole 6 of the ceramic guide 3 mounted on the predetermined measurement target site of the head. A substantially spherical support piece 23 made of resin is bonded to the wire electrode 2. The bonding position of the support piece 23 to the wire electrode 2 is determined such that when the wire electrode 2 is inserted in the ceramic guide 3, the support piece 23 is supported by a concave surface 16 described later in a state where the tip portion 2a of the wire electrode 2 has reached the predetermined measurement target site in the brain 24, and the wire electrode 2 is prevented from moving further in the distal direction (downward in FIG. 1). The concave surface 16 is curved or inclined toward the second portion 8 as approaching the central axis L1 from the outer edge 7a at the first end 4 of the first portion 7.

As a material of the support piece 23, for example, an epoxy resin can be used. The epoxy resin has a certain degree of viscosity and hardens into a ball shape after being attached to the wire electrode 2. Examples of the epoxy resin include "High—Super" (registered trademark) 5 two-component epoxy resin manufactured by CEMEDINE CO., LTD. Since this epoxy resin cures in about 5 minutes, the time required to form the support piece 23 on the wire electrode 2 can be short, providing a merit of good usability.

The wire electrode 2 mounted on the ceramic guide 3 includes a first protruding portion 25 projecting from the first end 4 of the ceramic guide 3, and a second protruding portion 26 projecting from the second end 5. The first protruding portion 25 is connected to a connector 31 described later, the connector 31 is connected to a lead wire 38, and the lead wire 38 is used to transmit the electrical activity information of the brain tissue to, for example, an electroencephalogram (abbreviated as EEG) device 30 (see FIG. 6) as a predetermined external device. The electroencephalogram device 30 may be realized with, for example, a personal computer.

The first portion 7, the second portion 8, and the third portion 9 have the common central axis L1 and are integrally formed of ceramics. An outer peripheral surface 10 of the second portion 8 has a smaller diameter than a diameter of the outer peripheral surface 11 of the first portion 7, and therefore a projection curve obtained when the outer peripheral surface 11 of the first portion 7 is projected on a virtual plane perpendicular to the central axis L1 is located radially outside of a projection curve of the outer peripheral surface 10 of the second portion 8 obtained when it is projected on the virtual plane perpendicular to the central axis L1. As a material of the ceramic guide 3, basically, any ceramics such as alumina ($Al_2O_3$), zirconia ($ZrO_2$), aluminum nitride (AlN), silicon carbide (SiC), silicon nitride ($Si_3N_4$), forsterite ($2MgO \cdot SiO_2$), sialon (SiAlON), barium titanate ($BaTiO_3$), lead zirconate titanate (PZT), ferrite and mullite can be used. Zirconia is particularly preferable due to the excellency in biocompatibility. The ceramic guide 3 may include an additive when the material is zirconia. Examples of the additive include a stabilizer such as yttria.

The ceramic guide 3 can be manufactured, for example, by the following steps. First, a powder of a ceramic raw material such as zirconia is kneaded with a thermoplastic binder to prepare a mixed material. Next, this mixed material is pressure-molded using a mold having a predetermined shape (space portion) of the ceramic guide 3 to prepare a produced body. Then, this produced body is sintered at a temperature of about 1300 to 1400° C. Through the above steps, the ceramic body 3 made of zirconia-containing ceramics can be manufactured.

Further, the curved or inclined concave surface 16 as described above can be formed by making the mold used for manufacturing the ceramic guide 3 to have the same shape as the concave surface 16. Alternatively, the concave surface 16 may be provided by producing the ceramic guide 3 having the first end 4 whose end surface is flat and then subjecting the end surface to post-processing such as polishing and grinding.

The outer peripheral surface 12 of the third portion 9 is curved in a direction approaching the central axis L1 from the peripheral edge 9a on the first portion 7 side to the peripheral edge 9b on the second portion 8 side. In another embodiment, the outer peripheral surface 12 of the third portion 9 may have a configuration inclined in a direction approaching the insertion hole 6 from the peripheral edge 9a on the first portion 7 side to the peripheral edge 9b on the second portion 8 side, that is, a shape forming an outer peripheral surface of a truncated cone. Such a curved shape of the outer peripheral surface 12 of the third portion 9 can also be formed by a method of adjusting the mold or carrying out post-processing, as in the case of the concave surface 16.

The first portion 7 includes the concave surface 16 that curves toward the second end 5 as approaching the central axis L1 from the outer edge 15. In another embodiment, the concave surface 16 may have a configuration inclined toward the second portion 8 side from the outer edge 15 toward the central axis L1, that is, a shape forming an outer peripheral surface of a truncated cone.

One example of each dimension of the ceramic guide 3 in the case where the activity information of the brain of the small experimental animal is measured is described below for the reference.

Diameter D1 of the outer peripheral surface 11 of the first portion 7: D1=1.25 mm Diameter D2 of the outer peripheral surface 10 of the second portion 8: D2=0.85 mm Inner diameter D3 of the insertion hole 6: D3=0.25 mm Diameter D4 of the concave surface 16 of the first end 15: D4=0.9 mm Elevation angle θ of concave surface 16: θ=90°

Total length L1: L1=3 mm

Length L2 of the first portion 7: L2=1.0 to 1.5 mm

Length L3 of second portion 8: L3=1.5 to 1.0 mm

Length L4 of third portion 9: L4=0.5 mm

The dimensions of the ceramic guide 3 are not limited to these, and in another embodiment, appropriate dimensions can be employed according to the type of measurement target, the target site, and the like.

As a material for the core wire of the wire electrode 2, the ceramic guide 3 uses single wires made of silver that are moderately soft and have a good shape retention, and therefore, a deviation of the penetrating wire electrode 2 from the insertion path that would occur when the wire electrode 2 is pierced into a dura mater 22 and the cerebral cortex of the brain 24 is reduced, the handling operability is excellent, and the indwelling operation becomes significantly easier and more accurate. Further, in the case of the silver wire, the shape can be changed flexibly by tweezers and the wire electrode 2 can be inserted in such a manner that it can be slid into the insertion hole 6 through the concave surface 16 of the ceramic guide 3. Therefore, the tip portion 2a of the wire electrode 2 can smoothly reach the measurement target site M in the brain 24 without causing a problem such as bending the wire during insertion.

The dura mater 22 is a tough membrane tissue, the cerebral cortex of the brain 24 is a brain tissue having a thickness of about 1 to 2 mm, and the tip portion 2a of the wire electrode 2 is guided to the insertion hole 6 along the concave surface 16 during the implant surgery. The operator grasps the wire electrode 2 using a pair of tweezers and manually places the tip portion 2a of the wire electrode 2 in the space where the support piece 23 is surrounded by the concave surface 16 and pushes the wire electrode 2 into the insertion hole 6. In this state, the support piece 23 of the wire electrode 2 abuts the concave surface 16, and then further penetration of the wire electrode 2 will be prevented. By pushing the wire electrode 2 in this way, the tip portion 2a of the wire electrode 2 can be easily and securely reached at the measurement target site M in the brain 24. As a result, a large-scale insertion operation of the wire electrode 2 using a manipulator is unnecessary, and the insertion operation of the wire electrode 2 can be easily carried out in a short time.

The core wire of the wire electrode 2 is not limited to the above-mentioned silver wire, and in other embodiments, as long as suitable handling can be realized for the insertion target site, tissue, insertion depth, a wire of tungsten, stainless steel, stainless alloy, or platinum, which have higher rigidity than silver, may be used for example. In the embodiment, a parallel electrode wire called "twisted-wire" is used, which is a bundle of two coated wires obtained by coating a silver core wire having an outer diameter of about 50 μm with a polytetrafluoroethylene (registered trademark: Teflon) resin. The outer diameter of the parallel electrode wire including the coating layer is about 110 μm. Further, a single electrode wire having the outer diameter of up to about 180 μm including the coating layer that is able to be slid into the insertion hole 6 can be used. When a single electrode wire is used, it is possible to measure the local field potential, one form of the electroencephalograms.

Figure 6:
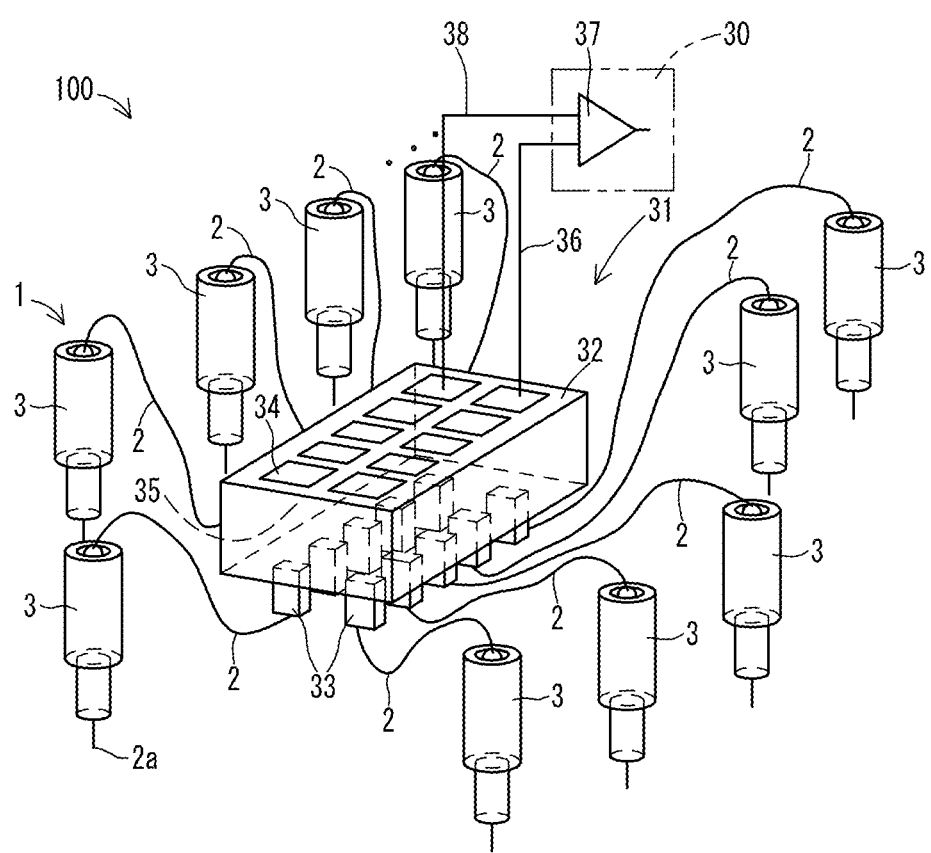
FIG. 6 is a perspective view showing a schematic configuration of a ceramic guide module.
Figure 7:
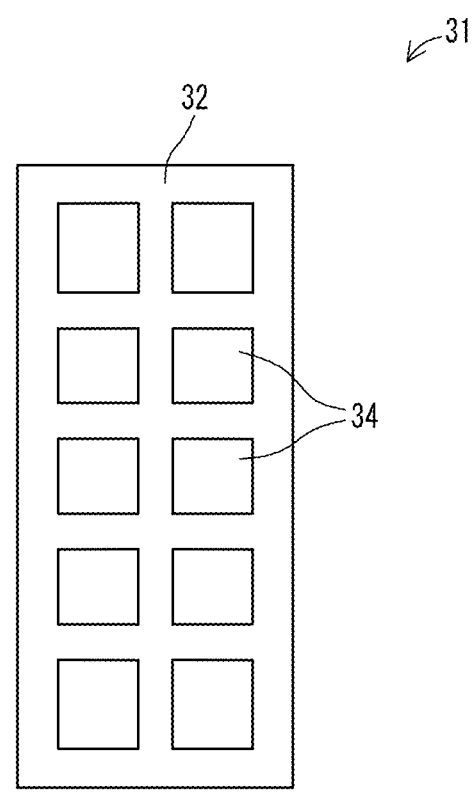
FIG. 7 is a plan view of a connector.

FIG. 6 is a perspective view showing a schematic configuration of the ceramic guide module, and FIG. 7 is a plan view of the connector. A ceramic guide module 100 of the embodiment is used as a system for sampling or modeling the activity information of the brain dynamics of a small animal in its normal or disease state. The ceramic guide module 100 includes a plurality (10 in the embodiment) of ceramic guides 3 with the wire electrode 2 inserted into each ceramic guides 3, and the connector 31 to which each wire electrode 2 is connected.

The connector 31 includes a substrate 32 made of an insulating material such as ceramics and an insulating resin, which is a plate-like body having a rectangular shape in a plan view, a plurality of input terminals 33 aligned on one surface of the substrate 32, a plurality of output terminals 34 aligned on the other surface of the substrate 32, and internal wirings 35 for individually connecting the input terminals 33 and the corresponding output terminals 34 inside the substrate 32.

One of the plurality of output terminals 34 is connected to one input terminal of a differential amplifier 37 by a lead wire 36. The remaining output terminals 34 are connected by lead wires 38 to the other input terminals of the differential amplifier 37, respectively. FIG. 6 shows only one lead wire 38 and omits the remaining lead wires 38 for ease of illustration. The differential amplifier 37 amplifies the difference between the reference signal inputted from the lead wire 36 to one input terminal and each measurement signal inputted from the lead wire 38 to the other input terminal of the differential amplifier 37, carries out predetermined signal processing such as waveform shaping and analog/digital conversion on the differential signal, and outputs the differential signal to the electroencephalogram device 30 as a measurement signal sampled for each wire electrode 2. The electroencephalogram device 30 includes a storage device and a display device, and the measurement signal output from the differential amplifier 37 is recorded in the storage device and displayed as a display image such as a signal waveform on the display screen of the display device.

Figure 8:
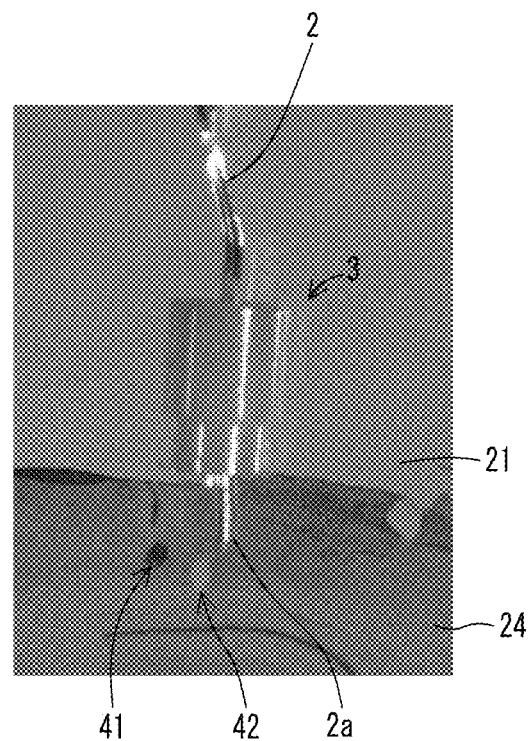
FIG. 8 is a view showing a state in which a ceramic guide and a wire electrode are placed on a rat brain section used in an experiment.
Figure 9:
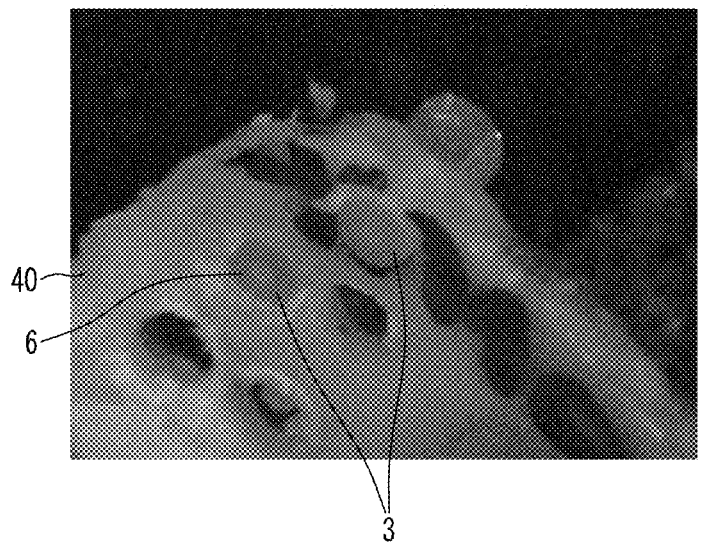
FIG. 9 is a view showing a state in which two ceramic guides are implanted in a rat skull fragment and viewed from the back side.

FIG. 8 is an image showing a state in which a ceramic guide and a wire electrode are placed over a rat brain section obtained from one experiment, and FIG. 9 is a view showing a state in which two ceramic guides are implanted in a rat skull fragment and viewed from the back side. The ceramic guide 3 is fixed to the head by inserting the ceramic guide into the holes formed through the scalp 20, the skull 21, and the dura mater 22 by aseptic surgery. The wire electrode 2 is inserted into the insertion hole 6 of the fixed ceramic guide 3, and the tip portion 2a of the wire electrode 2 is pierced into the tissue of the brain 24.

Finally, the ceramic guide 3 and the wire electrode 2 are firmly fixed to the skull 21 by covering them with a bonding material 27 made of, for example, dental cement. This allows the wire electrode 2 to be implanted into the brain 24 in a short time, for example, within a few tens of minutes, and be stably indwelled over a long period of time, for example, for 2 to 3 months, and information on the cerebral nerve activity, for example, information such as local field potential and action potentials can be stably recorded. At this time, the bonding material 27 may cover the wire electrode 2 and at least a part (the part on the skull side) of the connector 31 connected to the wire electrode 2. Further, the periphery of the bonding material 27 may be covered with the scalp 20.

While the number of the conventional guide device having a diameter of, for example, 5 mm or more is limited to at most two due to the space limitation, the ceramic guide 3 of the embodiment has a diameter of 1.25 mm or less, therefore a plurality of wire electrodes 2 can be placed therein, and brain activity information can be measured and recorded at multiple points. When the experimental small animal is a rat, at least sixteen wire electrodes 2 can be implanted.

The ceramic guide 3 is superior in that a special configuration is employed including the third portion 9 as a step, rather than a simple cylinder. Since the third portion 9 works as a stopper, it is possible to securely prevent the ceramic guide 3 from accidentally passing the skull 21 and the dura mater 22 during the implantation. The third portion 9 in any size can be produced with an accuracy of the order of microns by using our highly accurate ceramic processing technique.

Since the ceramic guide 3 includes the third portion 9, the third portion 9 is press-fitted into the rim of the opening of the scalp 20 and the skull 21 in the state where the second portion 8 is inserted into the scalp 20, the skull 21, and the dura mater 22, and thus it is possible to reduce the intrusion of the bonding material 27 and the like into the brain 24 through the gap between the ceramic guide 3 and the skull 21.

FIG. 9 shows a state in which two ceramic guides 3 are inserted in a rat skull fragment 40 (thickness: about 0.5 mm) and viewed from the back side (brain side). The step formed by the third portion 9 on the outer peripheral surface serves as a stopper, and the second portion 8 of the ceramic guide 3 can be prevented from protruding toward the brain 24 side and damaging the brain 24.

Figure 10:
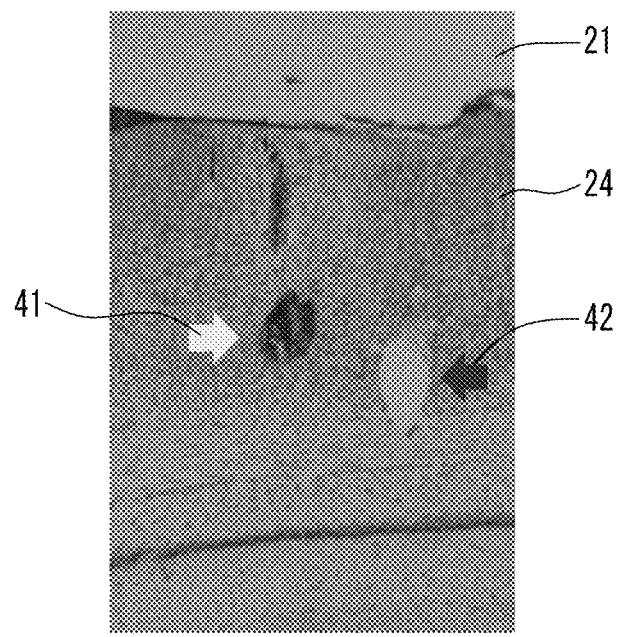
FIG. 10 is a view showing a state in which the ceramic guide and the wire electrode have been removed from the rat brain section used in an experiment.

Since the ceramic guide 3 is resistant to heat and chemicals, it is possible to sterilize or disinfect the ceramic guide by using an autoclave or by immersing the ceramic guide in a disinfectant solution. Further, as shown in FIG. 10, since no rejection reaction from the brain tissue is observed in the vicinity of the second portion 8 of the implanted ceramic guide 3, a long-term implant of the ceramic guide should be safe. The inventors have confirmed that no rejection reaction or the like had occurred one month after the implant. As illustrated by the arrow 41 in FIG. 10, by passing a small electric current through the wire electrode 2 after an experiment to make a tiny trace in the tissue of the brain 24, it was confirmed that the tip portion 2a of the wire electrode 2 was indeed in the cerebral cortex and the cortical surface was not greatly damaged. The hole indicated by the arrow 42 is the cavity of a cerebral blood vessel running nearby.

As described above, according to the ceramic guide 3 of the disclosure, since the third portion 9 is provided in the ceramic guide 3, the ceramic guide 3 can be easily attached to any attachment site such as a hole formed in the living body by grasping the ceramic guide 3 with tweezers without using a manipulator and therefore, the setting up time can be shortened. Since it does not take much time to insert the ceramic guide 3, the time necessary for restraining the living body is short, the adverse effect on the living tissue is small, and therefore, the burden on the living body can be minimized. Particularly when the attachment site is a hole formed on a bone surface, the second portion 8 of the ceramic guide 3 can be fitted into the hole. Therefore, the wire electrode 2, which is the insert, can be accurately positioned and fixed to the head together with the ceramic guide 3 due to the anchor effect of the second portion 8 to the hole, and the stability of attachment of the wire electrode 2 to the living body can be improved.

Further, according to the ceramic guide device 1 of the disclosure, the ceramic guide 3 utilizes a small hole for the wire electrode 2 in the living body, and the second portion 8 is fitted into the hole, whereby the ceramic guide 3 can be attached to the living body. Thus, it is possible to use an appropriate ceramic guide according to the type and size of the target animal, which allows improving the degree of freedom in the selection of the type of the wire electrode 2 capable of being attached to the living body.

Figure 11:
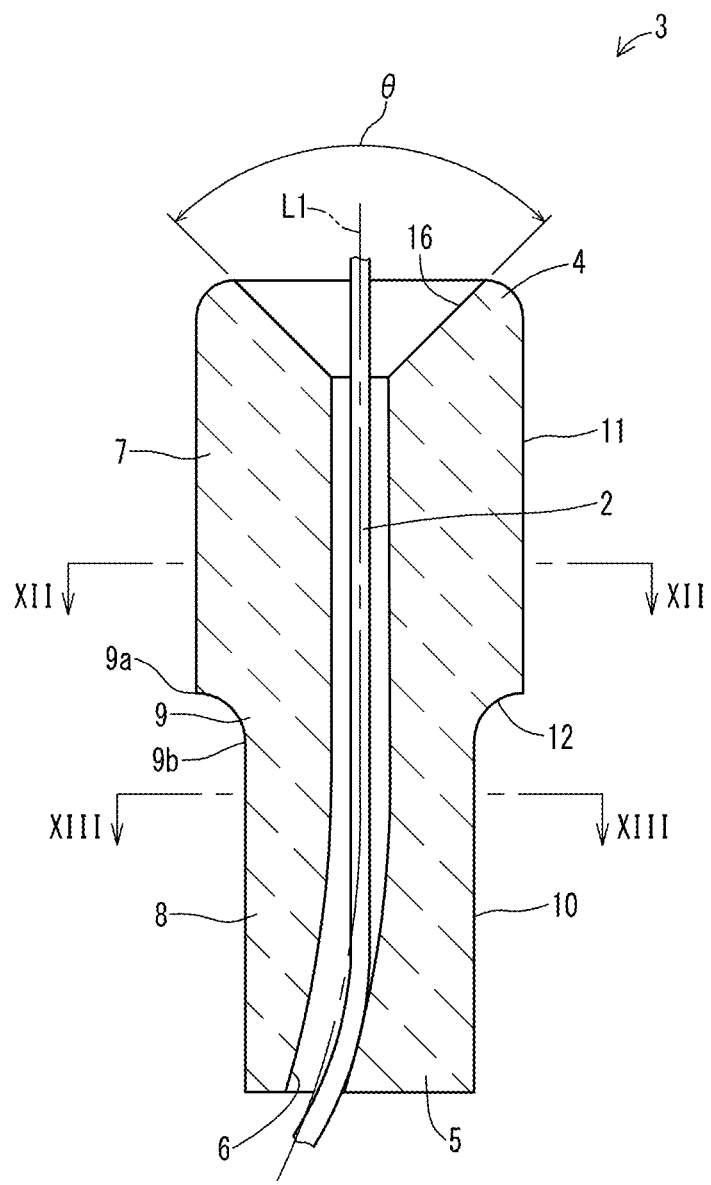
FIG. 11 is a cross-sectional view showing a ceramic guide according to another embodiment of the disclosure.
Figure 12:
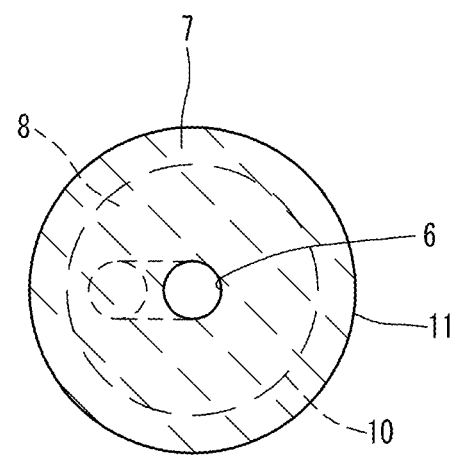
FIG. 12 is a cross-sectional view of the ceramic guide taken along the line XII-XII in FIG. 11.
Figure 13:
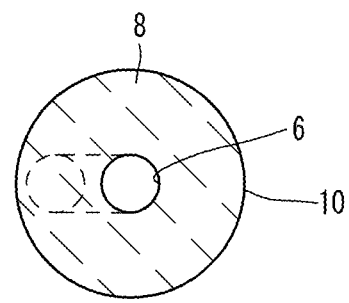
FIG. 13 is a cross-sectional view of the ceramic guide taken along the line XIII-XIII in FIG. 11.
Figure 14:
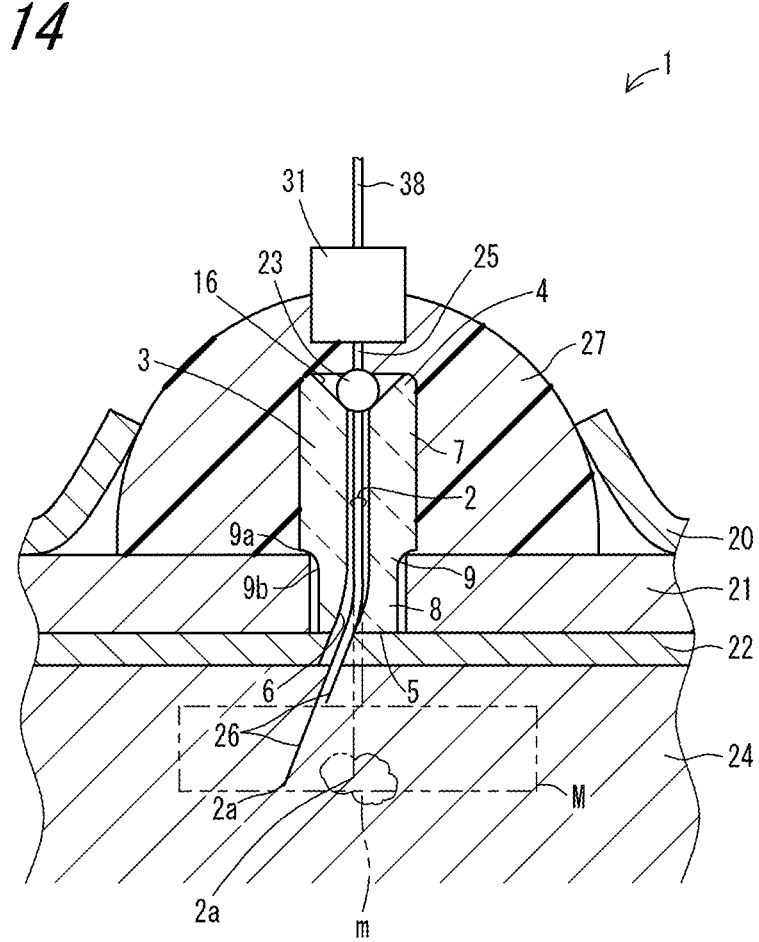
FIG. 14 is a partial cross-sectional view showing a ceramic guide module using the ceramic guide device shown in FIGS. 11 to 13.

FIG. 11 is a cross-sectional view showing a ceramic guide according to another embodiment of the disclosure, FIG. 12 is a cross-sectional view of the ceramic guide taken along the line XII-XII of FIG. 11, FIG. 13 is a cross-sectional view of the ceramic guide taken along the line XIII-XIII in FIG. 11, and FIG. 14 is a partial cross-sectional view showing a ceramic guide device using the ceramic guide shown in FIGS. 11 to 13. The components corresponding to those in the above-described embodiment are denoted by the same reference numerals, and the duplicated description will be omitted.

In the embodiment, the insertion hole 6 extends coaxially with the central axis L1 of the ceramic guide 3 in the first portion 7 and the third portion 9, and is formed to curve outward in the radial direction with advancing from the first end 4 to the second end 5 in the second portion 8.

By adopting such a configuration, even if the tissue M such as a nerve or a blood vessel exists in the brain 24 on the central axis L1, the tip portion 2a of the wire electrode 2 can be guided laterally so as to avoid the tissue M such as a nerve tissue or a blood vessel, and the damage to the tissue M can be prevented.

Figure 15:
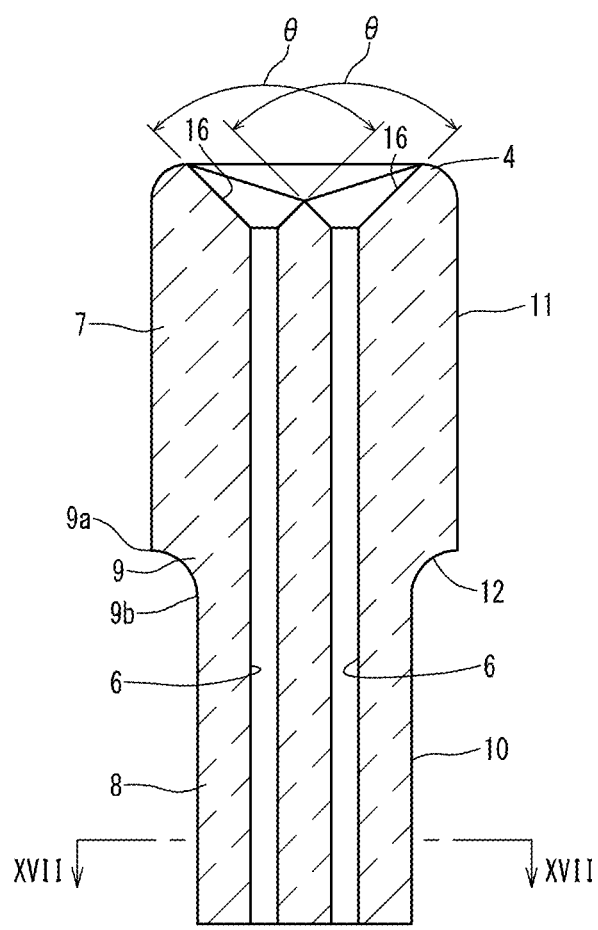
FIG. 15 is a cross-sectional view showing a ceramic guide according to still another embodiment of the disclosure.
Figure 16:
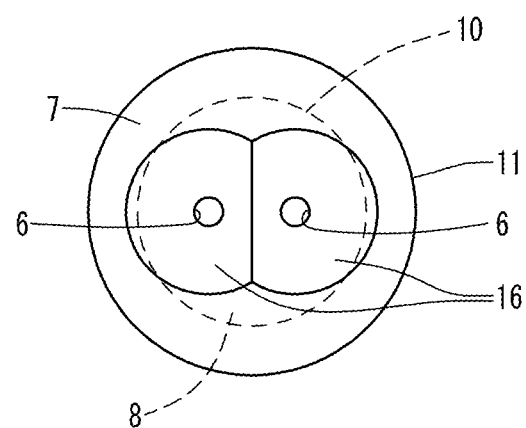
FIG. 16 is a plan view of the ceramic guide shown in FIG. 15.
Figure 17:
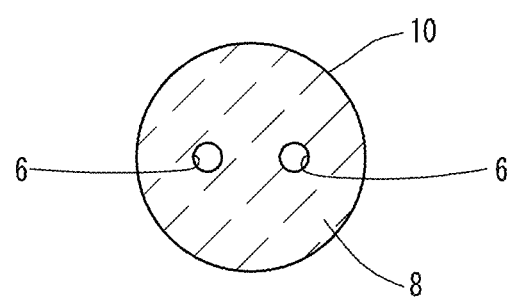
FIG. 17 is a cross-sectional view of the ceramic guide taken along the line XVII-XVII in FIG. 15.
Figure 18:
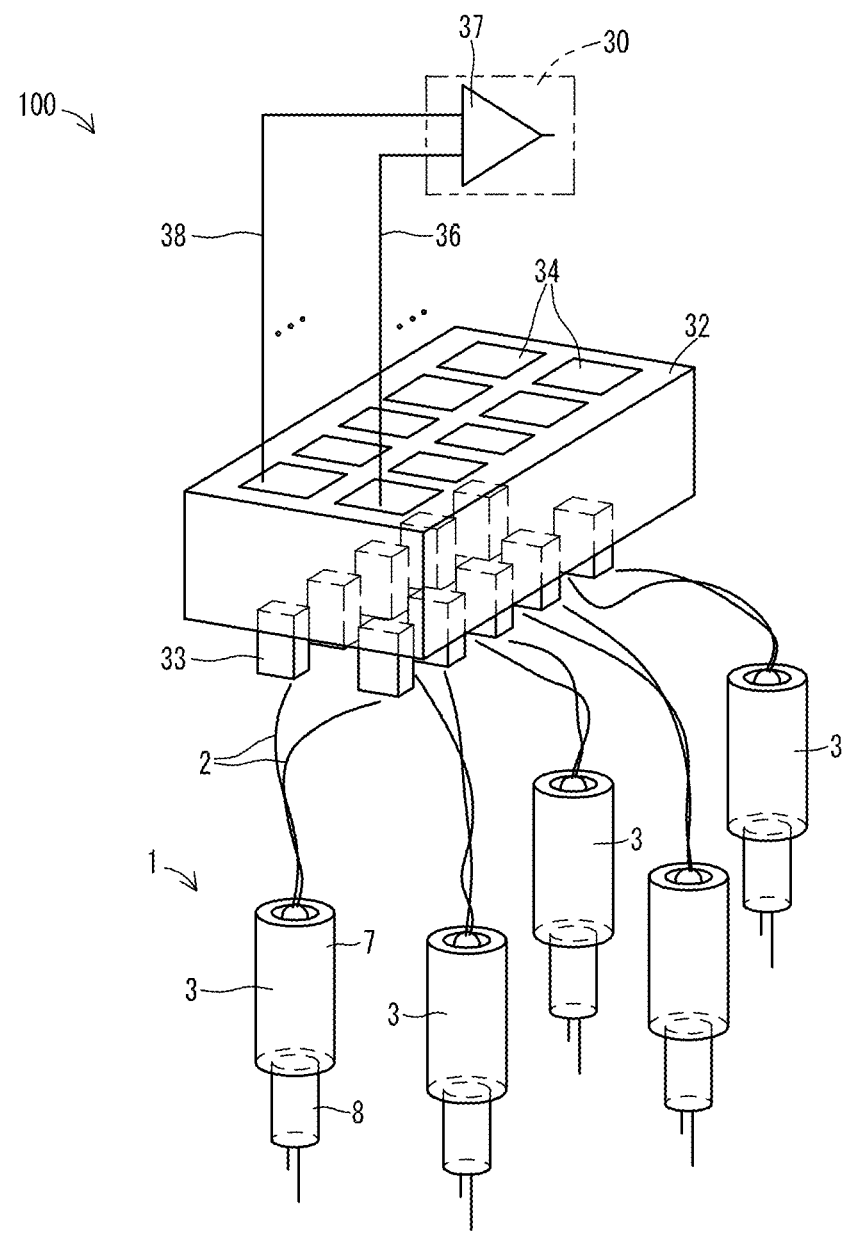
FIG. 18 is a partial cross-sectional view showing a ceramic guide device using the ceramic guide shown in FIGS. 15 to 17.

FIG. 15 is a cross-sectional view showing a ceramic guide according to still another embodiment of the disclosure, FIG. 16 is a plan view of the ceramic guide shown in FIG. 15, FIG. 17 is a cross-sectional view of the ceramic guide viewed from the line XVII-XVII of FIG. 15, and FIG. 18 is a partial cross-sectional view showing a ceramic guide device using the ceramic guide shown in FIGS. 15 to 17. The components corresponding to those in the above-described embodiment are denoted by the same reference numerals, and the duplicated description will be omitted.

In the embodiment, two insertion holes 6 are formed in the ceramic guide 3 symmetrically to the central axis L1. A single wire electrode 2 can be individually inserted into each insertion hole 6, and one can be used as a measurement electrode and the other as a reference electrode.

Figure 19:
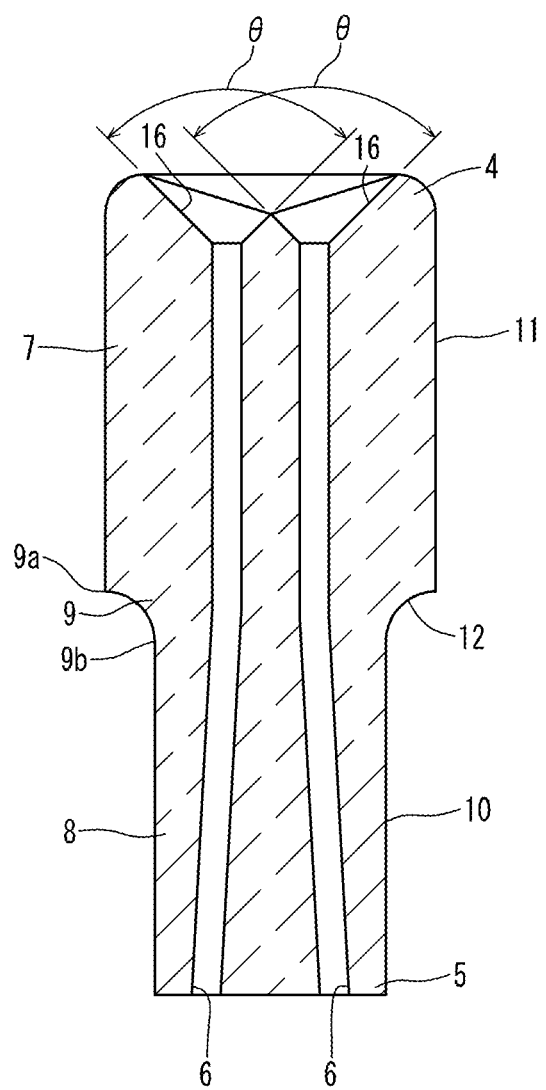
FIG. 19 is a cross-sectional view showing a ceramic guide according to still another embodiment of the disclosure.

As still another embodiment of the disclosure, as shown in FIG. 19, in the first portion 7 and the third portion 9, in the second portion 8, the two insertion holes 6 may be formed to be curved, such that they proceed away from each other. As a result, similarly to the above-described embodiment shown in FIGS. 15 to 18, each wire electrode 2 can be pierced into the brain 24 while avoiding the tissue M.

In still another embodiment of the disclosure, in the ceramic guide 3 described above, the outer peripheral surface 11 of the first portion 7 may be formed as a rough surface. As a method of roughening the outer peripheral surface 11 of the first portion 7, a blast method of spraying an abrasive may be used, or only the outer peripheral surface 11 of the first portion 7 may be chemically eroded by covering the outer peripheral surfaces 10 and 12 of the second and third portions 8 and 9 with mask materials and immersing the ceramic guide 3 in an etching solution to form a rough surface. It is also possible to carry out a roughening treatment by pressing a member such as a resin material with rough surface on the portion corresponding to the outer peripheral surface 11 of the first portion 7 of the formed body to be the ceramic guide 3 and then firing.

In the above-described embodiment, the scalp 20, the skull 21, the dura mater 22, and the brain 24 have been described as the target sites into which the wire electrode 2 is inserted or pierced, but in other embodiments of the disclosure, for example, any site in the living body may be targeted, where the wire electrodes 2 can be fixed with a bonding member similar to the bonding material 27. Further, examples of the insert may include a tube and a catheter, in addition to the wire electrode. In the case of a tube, liquid or gas can flow inside, and the convenience in use can be improved. In addition, the ceramic guide 3 may include a cross section perpendicular to the central axis L1 thereof with a shape of a polygon such as a circle, a rectangle, a triangle, or a pentagon. Further, the above-mentioned cross section of the ceramic guide 3 may be basically circular, but a part of its circumference may be linear or parts of its circumference may be axisymmetrically linear, that is, the cross section perpendicular to the axis may be D-shaped, substantially oval, or the like, and a flat surface portion may be provided on a part or two axisymmetrical portions of the peripheral surface of the first portion 7. When such a flat surface portion is provided, the ceramic guide 3 can be easily held with tweezers or other similar tools, and thus handling becomes easier.

In still another embodiment of the disclosure, a part of the outer peripheral surface of the first portion 7 may include a recessed portion 50 that is recessed toward the central axis L1 as shown by an imaginary line in FIG. 1. The bonding material 27 enters the recessed portion 50, and the displacement of the ceramic guide 3 due to such as rotation or slippage in the length direction (vertical direction in FIG. 1) can be reduced.

The disclosure may be embodied in other specific forms without departing from the spirit or essential characteristics thereof. The present embodiments are therefore to be considered in all respects as illustrative and not restrictive, the scope of the disclosure being indicated by the appended claims rather than by the foregoing description and all changes which come within the meaning and the range of equivalency of the claims are therefore intended to be embraced therein.

REFERENCE SIGNS LIST

1: Ceramic guide device
2: Wire electrode
3: Ceramic guide
4: First end
5: Second end
6: Insertion hole
7: First portion
8: Second portion
9: Third portion
9a: Peripheral edge on first portion 7 side
9b: Peripheral edge on second portion 8 side
L1: Central axis
10: Outer peripheral surface of second portion 8
11: Outer peripheral surface of first portion 7
12: Outer peripheral surface of third portion 9
15: Outer edge
16: Concave surface
30: Electroencephalogram device
31: Connector
32: Substrate
33: Input terminal
34: Output terminal
35: internal wiring
36, 38: Lead wire
37: Differential amplifier
100: Ceramic guide module

The invention claimed is:

1. A ceramic guide to be fixed to a living body, comprising:
a columnar ceramic body provided with an insertion hole through which a long insert can be inserted from a first end to a second end of the columnar ceramic body,
the columnar ceramic body comprising:
a first portion comprising the first end;
a second portion comprising the second end and having a smaller diameter than a diameter of the first portion; and
a third portion disposed between the first portion and the second portion, wherein the first end comprises a concave surface that is curved or inclined toward a second portion side from an outer edge of the first portion toward the insertion hole;
wherein the concave surface is connected to the insertion hole and is spaced from the third portion in a cross-sectional view perpendicular to a central axis of the insertion hole.

2. The ceramic guide according to claim 1, wherein an outer peripheral surface of the third portion is curved or inclined in a direction approaching the central axis from a peripheral edge on a first portion side of the third portion to a peripheral edge on a second portion side of the third portion.

3. The ceramic guide according to claim 1, wherein the second portion comprises zirconia.

4. The ceramic guide according to claim 1, wherein an outer peripheral surface of the first portion comprises a rough ceramic surface.

5. A ceramic guide device to be fixed to a living body, comprising:
the ceramic guide according to claim 1, and a long insert that penetrates through the insertion hole, the long insert comprising a first protruding portion projecting from a first end side of the insertion hole, and a second protruding portion projecting from a second end side of the insertion hole, the first protruding portion being connected to an external device, the second protruding portion being inserted into a living body.

6. The ceramic guide device according to claim 5, wherein the long insert comprises a wire electrode.

7. The ceramic guide device according to claim 6, wherein the wire electrode comprises a core wire comprising at least one of silver, gold, and platinum, and a resin coating layer that covers the core wire.

8. The ceramic guide device according to claim 5, further comprising:
   a resin support piece bonded to the first protruding portion;
   a size of the resin support piece is larger than a opening of the through hole, in plan view from a direction of the central axis; and
   the resin support piece is movable from the first end side of the insertion hole to a position where it contacts the concave surface.

9. A ceramic guide module, comprising:
   the ceramic guide device according to claim 5, and
   a connector to which the long insert is connected.

10. A ceramic guide to be fixed to a living body, comprising:
    a columnar ceramic body provided with an insertion hole through which a long insert can be inserted from a first end to a second end of the columnar ceramic body,
    the columnar ceramic body comprising:
       a first portion comprising the first end,
       a second portion comprising the second end and having a smaller diameter than a diameter of the first portion, and
       a third portion disposed between the first portion and the second Portion,
    wherein a part of an outer peripheral surface of the first portion comprises a recessed portion that is recessed toward a central axis of the ceramic guide.

* * * * *